(12) United States Patent
Freeman

(10) Patent No.: US 7,988,729 B2
(45) Date of Patent: Aug. 2, 2011

(54) HIGH ION AND METABOLITE FLUX LENSES AND MATERIALS

(75) Inventor: Charles Freeman, Granbury, TX (US)

(73) Assignee: Novartis AG, Basel (CH)

( * ) Notice: Subject to any disclaimer, the term of this patent is extended or adjusted under 35 U.S.C. 154(b) by 92 days.

(21) Appl. No.: 12/174,231

(22) Filed: Jul. 16, 2008

(65) Prior Publication Data

US 2009/0023835 A1    Jan. 22, 2009

Related U.S. Application Data

(60) Provisional application No. 60/950,782, filed on Jul. 19, 2007.

(51) Int. Cl.
*A61F 2/16* (2006.01)
*A61L 27/18* (2006.01)

(52) U.S. Cl. ........ 623/6.11; 623/6.13; 523/113; 524/555

(58) Field of Classification Search .................. 524/555; 523/113; 623/6.49, 6.36, 6.11, 6, 13
See application file for complete search history.

(56) References Cited

U.S. PATENT DOCUMENTS

| | | | |
|---|---|---|---|
| 3,220,960 A | 11/1965 | Wichterle et al. | |
| 3,532,679 A | 10/1970 | Steckler | |
| 3,792,028 A | 2/1974 | Seiderman | |
| 3,937,680 A | 2/1976 | de Carle | |
| 3,961,379 A | 6/1976 | Highgate | |
| 4,036,788 A | 7/1977 | Steckler | |
| 4,123,407 A | 10/1978 | Gordon | |
| 4,123,408 A | 10/1978 | Gordon | |
| 4,158,089 A | 6/1979 | Loshaek et al. | |
| 4,300,820 A | 11/1981 | Shah | |
| 4,402,887 A | 9/1983 | Kuriyama et al. | |
| 4,423,099 A | 12/1983 | Mueller et al. | |
| 4,430,458 A | 2/1984 | Tighe et al. | |
| 4,436,887 A | 3/1984 | Chromecek et al. | |
| 4,440,919 A | 4/1984 | Chromecek et al. | |
| 4,463,148 A | 7/1984 | Höfer et al. | |
| 4,680,336 A | 7/1987 | Larsen et al. | |
| 4,749,761 A | 6/1988 | Howes | |
| 4,866,148 A | 9/1989 | Geyer et al. | |
| 4,900,764 A | 2/1990 | Highgate et al. | |
| 5,039,459 A | 8/1991 | Kindt-Larsen et al. | |
| 5,147,394 A | 9/1992 | Siepser et al. | |
| 5,693,095 A * | 12/1997 | Freeman et al. | 623/6.56 |
| 6,015,609 A | 1/2000 | Chaouk et al. | |
| 6,060,530 A | 5/2000 | Chaouk et al. | |
| 6,107,365 A | 8/2000 | Bertozzi et al. | |
| 6,160,030 A | 12/2000 | Chaouk et al. | |
| 6,225,367 B1 | 5/2001 | Chaouk et al. | |
| 6,420,453 B1 | 7/2002 | Bowers et al. | |
| 6,635,731 B2 | 10/2003 | Mentak | |
| 2001/0018612 A1 * | 8/2001 | Carson et al. | 623/5.11 |
| 2005/0149184 A1 * | 7/2005 | Bogaert | 623/6.14 |

FOREIGN PATENT DOCUMENTS

| | | |
|---|---|---|
| GB | 2138589 A | 10/1984 |
| WO | 99/07309 | 2/1999 |
| WO | WO 9907309 A1 * | 2/1999 |
| WO | 02/069849 | 9/2002 |
| WO | WO 02069849 A1 * | 9/2002 |

OTHER PUBLICATIONS

International Search Report of a related PCT Application No. PCT/US2008/070176, mailed Sep. 26, 2008.
Written Opinion of the International Search Authority of a related PCT Application No. PCT/US2008/070176, mailed Sep. 26, 2008.

* cited by examiner

*Primary Examiner* — Michael M Bernshteyn
(74) *Attorney, Agent, or Firm* — Scott A. Chapple

(57) ABSTRACT

An exemplary embodiment provides a biocompatible polymer composition suitable for making intraocular lenses, especially posterior chamber phakic lenses, that includes a hydrogel having an equilibrium water content of less than about 55 wt. %. The hydrogel has a refractive index greater than about 1.41 and a sodium ion flux between about 16 to about 20 $\mu eq\text{-}mm/hr/cm^2$.

13 Claims, 1 Drawing Sheet

HIGH ION AND METABOLITE FLUX LENSES AND MATERIALS

This application claims priority to U.S. Provisional application, U.S. Ser. No. 60/950,782, filed Jul. 19, 2007.

TECHNICAL FIELD

The embodiments described herein generally relate to polymers that have a high metabolite flux, and more particularly relate to high ion and metabolite flux intraocular lens materials.

BACKGROUND

It is known that the human crystalline lens has active metabolic transport processes to maintain its health and clarity. It has been demonstrated that the crystalline lens contains sodium-potassium cellular pumps in the epithelial cells of the anterior half of the lens. These pumps are located from the anterior pole to the mid-periphery of the natural lens and it is known that the posterior half of the lens does not contain any pumps. There are sodium and potassium channels located around the entire surface of the lens. The flow of ions is necessary to maintain homeostasis in the ocular environment. A disruption in the circulation of ions throughout the crystalline lens could result in an imbalance in the system and lead to a cataract.

In some instances, when a patient encounters loss of visual acuity, implantation of an intraocular lens may be a recommended procedure. Because they facilitate less invasive surgery, soft intraocular lenses are preferred, wherever appropriate and possible. Generally, soft intraocular lenses are fabricated from two classes of materials: acrylics or silicones. Each of these materials may be hydrophilic or hydrophobic. When a material contains more than about 5% water under conditions of use, it is generally regarded as hydrophilic. Each material has found application in specific types of intraocular lenses. Common hydrogel components include N-vinyl-pyrrolidone (NVP) and hydroxyethyl methacrylate (HEMA), and the like. In some cases, the equilibrium water content appears to correlate with the permeability of the hydrogel. Thus, the higher the water content, the higher the expected ion and/or metabolite flux through the hydrogel.

In a special class of intraocular lenses, known as phakic intraocular lenses, which are implanted without removal of the natural lens, hydrogels are often preferred, especially in the case of posterior chamber phakic lenses where ion and metabolite flux is a consideration, as explained below. There are two major categories of phakic lenses: posterior chamber phakic lenses, which are implanted in the posterior chamber, just in front of the natural lens, and anterior phakic lenses which are implanted in the anterior chamber of the eye, in front of the iris.

Since phakic lenses are implanted without removal of the natural lens, the health of the natural lens must be maintained by an adequate supply of nutrients to maintain homeostasis. In the case of a posterior chamber phakic lens, the phakic lens body is interposed between the natural lens and the iris, and this may reduce or obstruct the flow of ions and/or metabolites in the vitreous to and from the natural lens. Lacking an adequate flow of ions and metabolites in the space between the phakic lens and the natural lens or through the body of the phakic lens, the risk of cataract formation increases. Because of their relatively higher ion flux as compared to hydrophobic lenses, hydrogels are the preferred lens material for posterior chamber phakic lenses. Higher ion flux through the synthetic phakic lens body permits a greater flow rate of ions and metabolites to and from the natural lens.

As pointed out above, higher ion and/or metabolite flux may in some instances correlate with high equilibrium water content. However, higher equilibrium water content typically also correlates with greater lens thickness, and thin lenses are more desirable. Accordingly, a balance must be struck between the desire for a high ion and metabolite flux through the lens and the desired lens thickness.

Accordingly, it is desirable to develop a material that has a high ion and metabolite flux, that is biocompatible and that is suitable for use as a phakic intraocular lens material. In addition, it is desirable to develop a material that has high ion and metabolite flux and relatively low water content to enable thinner intraocular lenses. Furthermore, other desirable features and characteristics of the high ion and metabolite flux lenses and materials will become apparent from the subsequent detailed description and the appended claims, taken in conjunction with the accompanying drawings and the foregoing technical field and background.

BRIEF SUMMARY

An exemplary embodiment provides a biocompatible polymer composition that includes a hydrogel having an equilibrium water content of less than about 55 wt. %. The hydrogel has a refractive index greater than about 1.41 and an ion flux greater than about 16 $\mu$eq-mm/hr/cm$^2$.

Another exemplary embodiment provides a polymeric composition that includes a polymerization product of from about 68 to about 71 wt. % N-vinyl-pyrrolidone and about 28 to about 30 wt. % 2-phenyl ethyl methacrylate. The polymerization product has a refractive index greater than about 1.41 and an equilibrium water content of less than about 55 wt. %.

Another exemplary embodiment provides a phakic posterior chamber intraocular lens that is made of a polymerization product of from about 68 to about 71 wt. % N-vinyl-pyrrolidone and about 28 to about 30 wt. % 2-phenyl ethyl methacrylate. The polymerization product has a refractive index greater than about 1.41 and an equilibrium water content of less than about 55 wt. %. In addition, it may have an ion flux between about 16 to about 20 $\mu$eq-mm/hr/cm$^2$.

DETAILED DESCRIPTION

Figure 1:
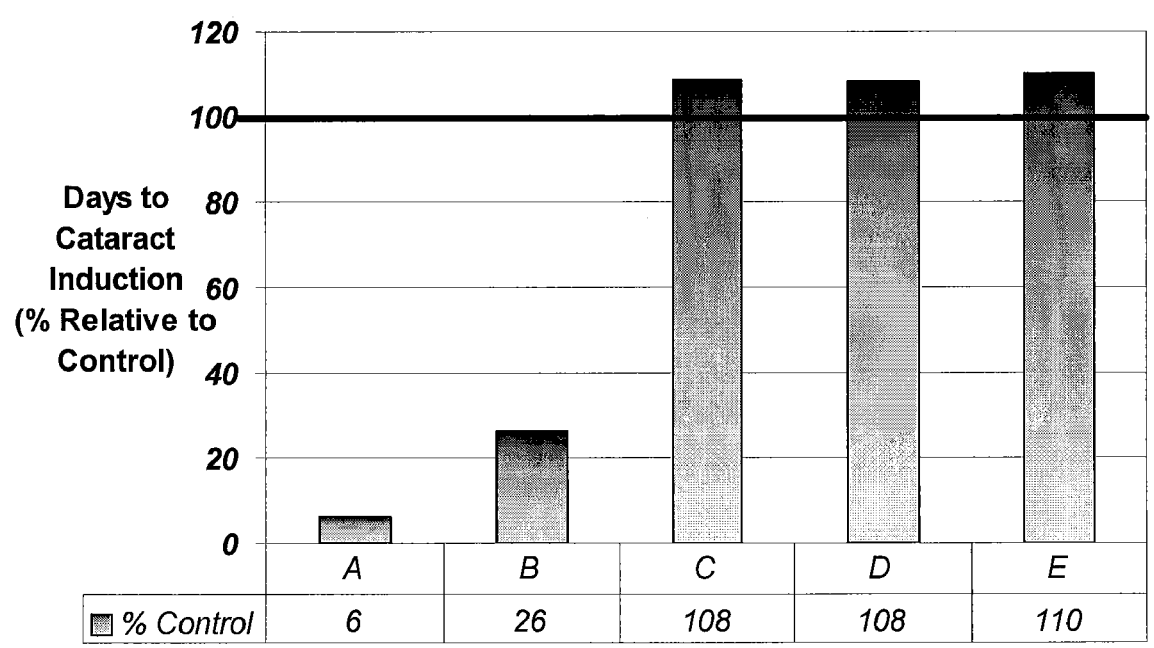
FIG. 1 is a bar graph illustrating the effect of ion flux on the ability of a lens material to avoid causing cataract formation in a rabbit lens.

The following detailed description is merely exemplary in nature and is not intended to limit the described embodiments or the application and uses of the described embodiments. Furthermore, there is no intention to be bound by any expressed or implied theory presented in the preceding technical field, background, brief summary or the following detailed description.

In the specification and claims, the term "ion flux" means the total flux determined by separately measuring the sodium flux and the chloride flux then adding the two together. A high ion flux refers to a flux of greater than or equal to about 16 $\mu$eq-mm/hr/cm$^2$. Ion flux may be measured by the technique described here below.

As a preliminary matter, one of the primary design strategies for posterior chamber phakic lenses involves locating the lens as far as possible away from the crystalline lens in a static situation. This may result in a lens that pushes the iris deep into the anterior chamber. Thus, the designs allow the implanted phakic lens to float above the natural crystalline lens leaving a fluid layer between the two for metabolites to flow to and from the natural lens. It is generally believed that placing a phakic lens in close proximity to the natural crystalline lens could disrupt metabolite flow to such an extent that it could or would result in cataractogenesis. This belief is confirmed in many of the clinical studies.

Embodiments of the present technology, on the contrary, present high ion flux lens materials that are so permeable to metabolites of the eye that phakic lenses of these materials may be placed in close proximity to the natural lens thereby minimizing any displacement of the iris while also permitting high ion flux through the phakic lens materials to the natural lens. Accordingly, the present lens materials have a sufficiently high ion permeability to provide a metabolic pathway through the lens body to the natural crystalline lens.

In an exemplary embodiment, a biocompatible high ion flux and high metabolite flux material is suitable for making posterior chamber phakic intraocular lenses. The material has an equilibrium water content of less than about 55 wt. %. Accordingly, it is eminently suitable for forming thin, high flux posterior chamber phakic intraocular lenses. In addition, the material is foldable for ease of insertion into the eye using an intraocular lens injector, and has sufficient elasticity to readily "spring back" to a lens shape once in the eye. Further, the lens material is sufficiently stiff or rigid to maintain the lens in its location in the eye after implantation. While some embodiments of the material may be too rigid at low temperatures to be foldable, at about 30° C. the material is flexible and foldable to fit into an intraocular lens injector for intraocular lens insertion.

When water is added to hydrate exemplary embodiments of the gel to form the hydrogel, the gel swells by about 30 vol. %. Note that in the specification and claims, the term "equilibrium water content" or "EWC" refers to water content obtained by the following method. The dry polymer material is weighed on a balance and the dry weight is recorded. The polymer is then placed into a vial that is filled with de-ionized water or a balanced salt solution. The vial is placed into a water bath and allowed to equilibrate at the desired temperature. After about 24 hours the polymer is removed from the water and any adhering surface water is removed by drying with a tissue. The tissue-dried polymer is weighed to obtain the hydrated weight. The equilibrium water content is calculated as: [(hydrated weight−dry weight)/hydrated weight wet]×100=EWC wt. %.

In order to characterize the permeability of a hydrogel, a membrane diffusion technique uses radio-isotopes to monitor the passage of sodium and chloride through the hydrogel. Briefly, after determining the thickness, each hydrogel lens test sample is clamped between two Teflon disks each of which has a central 3 mm opening for fluid diffusion. The clamped assembly is mounted between two glass diffusion cells, each of which has an internal volume of 3 ml and enclosed by a water jacket. During assay, a circulating water bath is used to maintain the temperature at 37° C. The diffusion cells are placed on a magnetic stirrer that activates a magnetic stirrer pellet inside each diffusion chamber. The chambers are filled with 3 ml of BSS (balanced salt solution). At time zero, $Cl^{36}$ is added to cell A (hot side) to a final concentration of 1 µCi/ml. At 30, 45, 60, and 75 min, 0.3 ml of BSS from cell B (cold side) is removed for β-radioactivity counting, by mixing with liquid scintillation solution. An equal volume of fresh BSS is added back to cell B each time. Immediately after the last collection, $Na^{22}$ is added to cell A to a final concentration of 2 µCi/ml. The collection of BSS in cell B is repeated at the same time intervals, as above, and each volume is counted for γ-radioactivity without further treatment. A 5 µl volume of radioactive solution in cell A is removed at the start and end of each isotope cycle for measuring the specific radioactivity (cpm/µEq). The microequivalents (µEq) of Na and Cl are calculated from the total Na and Cl concentrations in the BSS. The time kinetics of Na and Cl flux are separately plotted for each test sample and the ionic flux of µEq/hr is measured for each ion. The total ionic flux coefficient are calculated from the sum of the Na and Cl fluxes, and expressed as $\mu Eq/hr\text{-}cm^2$.

In a preferred embodiment, the composition of the lens material includes a copolymer of N-vinyl-pyrrolidone (NVP) and 2-phenyl ethyl methacrylate (PEMA) crosslinked with a cross-linking agent, for example, allyl methacralate (AMA). An exemplary embodiment of the high ion flux composition is as follows:
NVP about 68 to about 71 wt. %, preferably about 70 wt. %
PEMA about 28 to about 31 wt. %, preferably about 29 wt. %
AMA about 0.1 to about 1.0 wt. %

Preferably, exemplary embodiments of the lens materials have an equilibrium water content of less than about 55 wt. %, a refractive index of greater than about 1.41 and a total sodium and chloride ion flux of between about 16 to about 20 µeq-mm/hr/$cm^2$.

The high refractive indices of these exemplary embodiments of the hydrogels, coupled with low equilibrium water content, permit the fabrication of high flux posterior chamber phakic lenses that may be positioned in closer proximity to the natural lens than phakic lenses of lower ion flux without significantly increased risk of cataractogenesis. Indeed, in vitro cataractogenesis tests with rabbit lenses (described in the examples below), demonstrate that the high ion flux materials have markedly superior performance with respect to avoiding cataractogenesis. One of each of multiple pairs of rabbit lenses were covered with a lens of an exemplary embodiment of the high flux materials and the other lens was an uncovered control. The covered lenses met at least 100 percent of control by remaining cataract-free for as long as its uncovered pair. In addition, as a consequence of the high ion flux and high metabolite flux, coupled with high refractive index and low equilibrium water content, the lens materials may be used to make thin intraocular lenses of all kinds. Not only do exemplary embodiments of these materials provides a sufficiently high ion and metabolite flux to maintain the health of the natural lens and reduce the risk of cataract formation, but the materials also are foldable for insertion of a lens using a lens injector and are also sufficiently stiff once implanted to remain in position.

The high flux hydrogel lens materials may be made by any of a variety of methods. In one exemplary embodiment, hydrogels may be made by mixing monomer components and an initiator and then pouring the mixture into lens mold cavities. The liquid formulation may then be polymerized. In some embodiments, the liquid may be thermally cured and in others they may be polymerized using ultraviolet light.

Once formed, the hydrogels may be cut into the lens shape using a lathing process or may be prepared using a cast molding technique. In this process the molds themselves define the shape of the lens and do not require lathe operations.

The following examples are merely illustrative and do not limit the scope of the embodiments as herein described and claimed.

EXAMPLES

The following example illustrates a general methodology used for testing time to cataractogenesis of a natural lens, and "percent of control" for lenses covered with a hydrogel material.

Rabbit corneas are used to test for cataractogenesis. Both crystalline lenses from a single New Zealand White (NZW) female rabbit are enucleated after $CO_2$ asphyxiation. The lenses should be carefully dissected from the globe using aseptic conditions and placed onto a support holder with the anterior pole facing up. The support holder should be designed to provide circumferential support for the lenses above the container base. This allows each lens to be bathed in solution throughout the experiment. Care should be exercised to avoid metal instrument contact or other damaging contact with the lens. The container may be a standard 6 well culture dish that will contain each of the two lenses from the single rabbit. Each lens is covered in about 11 mls of an aqueous medium that contains Earles' salts and Fetal Bovine Serum to a 4% concentration in addition to stock solutions of L-glutamine, and penicillin/streptomycin (at final concentrations of 0.2 mM and 100 units penicillin/0.1 mg streptomycin per milliliter). The aqueous medium should be totally replaced every other day. Each day the lenses should be visually inspected for clarity and or opacity. If an opacity is detected, the location (whether posterior or anterior) and extent of coverage noted. The total number of days without opacity is counted, not including the day the opacity was first noted.

Comparative Example

A control study was conducted where 20 eyes from 10 rabbits were subjected to the above described test procedure. These lenses did not have any synthetic lens covering them. The results indicated that after discarding the obvious outliers, both eyes from the same rabbit respond similarly. Thus, it should be possible to compare lenses of paired eyes (i.e., eyes from the same rabbit) with and without synthetic lenses on actual tests.

Using the above-described methodology, cataractogenesis tests were conducted using embodiments of the present high ion flux lens material. For each of multiple pairs of natural rabbit lenses, a synthetic lens made of an embodiment of the high ion flux hydrogel materials of the present technology completely encompassed the anterior globe of one of the pair of rabbit lenses, while the other natural rabbit lens was an uncovered control. The synthetic lenses were designed with a posterior radius that would match an average rabbit lens radius and had a constant thickness of approximately 400 µm. Lenses of comparative materials A and B were used in some tests while exemplary embodiments of the present technology C, D and E were used in others. The compositions of the synthetic lens materials used were as follows:

Composition A=cross linked polyhydroxy ethyl-methacrylate (PHEMA)

Composition B=51.53% N-vinyl-pyrrolidone, 44.01% phenylbutyl methacrylate, 3.98% benzotriazol hydroxyethyl methacrylate and allyl methacrylate.

Compositions C and D were both=70% N-vinyl-pyrrolidone, 24.5% PEMA, 5.0% benzotriazol hydroxyethyl methacrylate and 0.5% allyl methacrylate.

Composition E=35% N-vinyl-pyrrolidone, 64.5% 2-hydroxyethyl methacrylate, and 0.5% allyl methacrylate.

The results of testing time to cataractogenesis are shown in FIG. 1. It is apparent that the high ion flux lenses performed markedly better than lenses of other materials. For a pair of rabbit lenses, the rabbit lens covered with an embodiment of the high ion flux material of the present technology was cataract-free for as long as its uncovered control lens.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient road map for implementing the exemplary embodiment or exemplary embodiments. It should be understood that various changes can be made in the function and arrangement of elements without departing from the scope as set forth in the appended claims and the legal equivalents thereof.

What is claimed is:

1. A biocompatible polymer composition comprising: a hydrogel having an equilibrium water content of from 50 to 55 wt. %, a refractive index greater than about 1.41 and a total sodium and chloride ion flux from about 16 µeq-mm/hr/cm$^2$ to about 20 µeq-mm/hr/cm$^2$, wherein: i) the hydrogel is formed into a thin, high flux posterior chamber intraocular phakic lens; ii) the hydrogel includes N-vinyl-pyrrolidone and 2-phenyl ethyl methacrylate crosslinked with a crosslinking agent; iii) the intraocular phakis lens is foldable for insertion into a lens injector; and iv) the intraocular phakic lens of the hydrogel is sufficiently rigid to remain in an implanted position within a posterior chamber of an eye interposed between a natural lens and an iris of the eye.

2. The biocompatible polymer of claim 1, wherein the hydrogel comprises about 70 wt. % N-vinyl-pyrrolidone and about 29 wt. % 2-phenyl ethyl methacrylate.

3. The biocompatible polymer composition of claim 2, wherein the hydrogel swells about 30 vol. % upon hydration.

4. The biocompatible polymer composition of claim 3, wherein the crosslinking agent comprises from about 0.2 to about 1.0 wt. % of allyl methacrylate.

5. A polymeric composition comprising: a polymerization product consisting essentially of from about 68 to about 71 wt. % N-vinyl-pyrrolidone and from about 28 to about 30 wt. % 2-phenyl ethyl methacrylate crosslinked with a crosslinking agent, the polymerization product having a refractive index greater than about 1.41 and an equilibrium water content that is in a range of 50 to 55 wt. % wherein: i) the polymerization product is formed into a thin, high flux posterior chamber intraocular phakic lens: ii) the sodium ion flux is between about 16 to about 20 µeq-mm/hr/cm$^2$: iii) the intraocular phakis lens is foldable for insertion into a lens injector; and iv) the intraocular phakic lens of the hydrogel is sufficiently rigid to remain in an implanted position within a posterior chamber of an eye interposed between a natural lens and an iris of the eye .

6. The polymer composition of claim 5, wherein the equilibrium water content is about 52 wt. %.

7. The polymer composition of claim 5, wherein the crosslinking agent comprises from about 0.2 to about 1.0 wt. % of allyl methacrylate.

8. The polymer composition of claim 5, further comprising an ultraviolet light absorber.

9. A phakic posterior chamber intraocular lens comprising a hydrogel polymerization product of from about 68 to about 71 wt. % N-vinyl-pyrrolidone and from about 28 to about 30 wt. % 2-phenyl ethyl methacrylate crosslinked with a crosslinking agent, the polymerization product having a refractive index greater than about 1.41 and an equilibrium water content of from 50 to 55 wt. % wherein: i) the polymerization product is formed into a thin, high flux posterior chamber intraocular phakic lens; ii) the intraocular phakis lens is foldable for insertion into a lens injector; and iii) the intraocular phakic lens of the hydrogel is sufficiently rigid to remain in an implanted position within a posterior chamber of an eye interposed between a natural lens and an iris of the eye.

10. The phakic posterior chamber lens of claim 9, wherein the polymerization product comprises about 70 wt % N-vinyl-pyrrolidone, and about 29 wt. % 2-phenyl ethyl methacrylate and an equilibrium water content of about 52 wt. %.

11. The phakic posterior chamber lens of claim 9, wherein a total sodium and chloride ion flux of the phakic posterior chamber lens is between about 16 to about 20 μeq-mm/hr/cm$^2$.

12. The biocompatible polymer composition of claim 1 wherein the hydrogel swells about 30 vol. % upon hydration.

13. The biocompatible polymer composition of claim 9 wherein the polymerization product swells about 30 vol. % upon hydration.

* * * * *

UNITED STATES PATENT AND TRADEMARK OFFICE
CERTIFICATE OF CORRECTION

PATENT NO. : 7,988,729 B2  
APPLICATION NO. : 12/174231  
DATED : August 2, 2011  
INVENTOR(S) : Charles Freeman It is certified that error appears in the above-identified patent and that said Letters Patent is hereby corrected as shown below:

Col. 6, ln. 54, delete "eve" and insert --eye--

Signed and Sealed this  
Twenty-seventh Day of September, 2011

David J. Kappos  
*Director of the United States Patent and Trademark Office*